United States Patent
Donavon et al.

(10) Patent No.: US 9,420,809 B2
(45) Date of Patent: Aug. 23, 2016

(54) SYSTEMS AND METHODS FOR ORDERING AND MANUFACTURING CUSTOM PET FOOD

(71) Applicant: NESTEC SA, Vevey (CH)

(72) Inventors: Mark A Donavon, Troy, IL (US);
Mark A Roos, Columbia, IL (US);
Brian Lester, St. Louis, MO (US)

(73) Assignee: Nestec SA, Vevey (CH)

( * ) Notice: Subject to any disclaimer, the term of this patent is extended or adjusted under 35 U.S.C. 154(b) by 92 days.

(21) Appl. No.: 14/208,840

(22) Filed: Mar. 13, 2014

(65) Prior Publication Data

US 2014/0272028 A1 Sep. 18, 2014

Related U.S. Application Data

(60) Provisional application No. 61/788,000, filed on Mar. 15, 2013.

(51) Int. Cl.
*A23K 1/18* (2006.01)
*G06F 17/30* (2006.01)
(Continued)

(52) U.S. Cl.
CPC . *A23K 1/18* (2013.01); *A23K 1/16* (2013.01); *A23K 1/1846* (2013.01); *G06F 17/30424* (2013.01); *G06Q 10/087* (2013.01); *G06Q 50/04* (2013.01)

(58) Field of Classification Search
CPC ......... A23K 1/00–1/001; A23K 1/16–1/1758; A23K 1/1846–1/1866; G06Q 10/087; G06Q 50/04; G06F 17/30424
USPC ........................................ 426/231, 519, 805
See application file for complete search history.

(56) References Cited

U.S. PATENT DOCUMENTS 6,156,355 A * 12/2000 Shields, Jr. ............... A23K 1/10
426/61
6,358,546 B1 3/2002 Bebiak et al.
(Continued)

FOREIGN PATENT DOCUMENTS

AU 2008203273 8/2005
JP 2006174734 7/2006
(Continued)

OTHER PUBLICATIONS

International Search Report & Written Opinion, PCT/US2014/25907; dated Jul. 8, 2014.
(Continued)

*Primary Examiner* — Drew Becker
(74) *Attorney, Agent, or Firm* — Ronald A. Burchett; Julie M. Lappin

(57) ABSTRACT

Methods and systems for customized pet food are described. Generally, the systems and methods comprises obtaining a pet profile information from a user, which includes at least one of a species, an activity level, a medical history, a breed, a gender, a breeding status, a feeding method, an age, a spayed/neutered status, a snack schedule, a biological sample, a body condition, a dental health, a coat information, a digestive health information and a weight of the pet. The methods and systems may also comprise obtaining a second pet profile information from a user, related to a preference regarding an ingredient, a food form, a flavor, a protein source, a shape and a texture. The methods and systems also may include correlating the first pet profile information and second pet profile information to a stored nutritional information to determine a pre-made pet blend based.

8 Claims, 10 Drawing Sheets

(51) Int. Cl.
*G06Q 10/08* (2012.01)
*A23K 1/16* (2006.01)
*G06Q 50/04* (2012.01)

(56) References Cited

U.S. PATENT DOCUMENTS

| | | | | |
|---|---|---|---|---|
| 6,493,641 | B1* | 12/2002 | Singh | A23K 1/1846 |
| | | | | 426/805 |
| 6,576,280 | B2* | 6/2003 | Bebiak | A01K 5/02 |
| | | | | 426/231 |
| 6,669,975 | B1* | 12/2003 | Abene | A23K 1/001 |
| | | | | 426/2 |
| 8,234,099 | B2* | 7/2012 | Dodds | G06F 19/3475 |
| | | | | 703/11 |
| 2002/0004749 | A1 | 1/2002 | Froseth et al. | |
| 2006/0036419 | A1* | 2/2006 | Cook | A01K 5/02 |
| | | | | 705/300 |
| 2006/0045909 | A1* | 3/2006 | Friesen | A23K 1/001 |
| | | | | 424/442 |
| 2006/0062892 | A1* | 3/2006 | Merrick | A23K 1/10 |
| | | | | 426/635 |
| 2006/0200320 | A1* | 9/2006 | Al-Murrani | G06F 19/3475 |
| | | | | 702/20 |
| 2006/0240150 | A1* | 10/2006 | Delaney | A23L 1/293 |
| | | | | 426/74 |
| 2007/0118295 | A1* | 5/2007 | Al-Murrani | G06F 19/18 |
| | | | | 702/19 |
| 2008/0243501 | A1 | 10/2008 | Hafsteinsson et al. | |
| 2014/0141134 | A1* | 5/2014 | Johnson | A23K 1/001 |
| | | | | 426/231 |

FOREIGN PATENT DOCUMENTS

| | | |
|---|---|---|
| JP | 2007209322 | 8/2007 |
| JP | 2002197290 | 7/2012 |
| WO | 01/69487 | 9/2001 |

OTHER PUBLICATIONS

European Search Report for Appl No. 14768538.2 dated Feb. 15, 2016—8 pages.

Communication from the European Patent Office for Appl No. 14768538.2 dated Mar. 3, 2016—1 page.

* cited by examiner

Cluster Type A Wellness Variables Priority Listing

| |
|---|
| Optimal protein and fat levels to help pets maintain healthy weight and ideal body condition |
| EPA, an omega-3 fatty acid, and glucosamine to help support joint health and mobility |
| Omega-6 fatty acids and zinc to help nourish skin and promote a healthy coat |
| Hard kibble texture to help reduce plaque build-up on teeth |
| DHA from omega-rich fish oil to help nourish brain and vision development |
| High-quality sources of carbohydrates for sustained energy |
| Real meat |
| Easily digestible formula to help be gentle on the digestive system |

Cluster Type B Wellness Variables Priority Listing

| |
|---|
| Omega-6 fatty acids and zinc to help nourish skin and promote a healthy coat |
| Easily digestible formula to help be gentle on the digestive system |
| High-quality sources of carbohydrates for sustained energy |
| DHA from omega-rich fish oil to help nourish brain and vision development |
| EPA, an omega-3 fatty acid, and glucosamine to help support joint health and mobility |
| Optimal protein and fat levels to help pets maintain healthy weight and ideal body condition |
| Hard kibble texture to help reduce plaque build-up on teeth |
| Real meat |

FIG. 6

| Base Kibble | Chicken | Lamb | Salmon |
|---|---|---|---|
| A | A1 | A2 | A3 |
| B | B1 | B2 | B3 |
| BGF | BGF1 | BGF2 | BGF3 |
| C | C1 | C2 | C3 |

FIG. 7

| Q. # | Req. | Label | Options | Option Weight |
|---|---|---|---|---|
| 1 | X | A good | Boy, Girl | None |
| 2a | X | Approximately + Q2a + old and weighs + Q2b + lbs. | Less than 6 months, 6 months to 1 year, 1 year, 2 years, 3 years, 4 years, 5 years, 6 years, 7 years, 8 years, 9 years or more | |
| 2b | X | Part of 2a | Text Input | None |
| 3a | X | What type of dog is "Dog Name"? | See List | None |
| 3b | X | | Toy, Small, Medium, Large, Giant | |
| 4 | X | I would describe "Dog Name" as: | Less Active, Semi-active, Active, Highly Active | |
| 5 | X | | Underweight, Ideal Weight, Overweight | None |
| 6 | X | "Dog Name" eats food: | Begrudgingly, Casually over time, Eagerly & Immediately | None |
| 7 | X | When getting to his feet, "Dog Name" is: | Slow & Cautious, Casual & Relaxed, Quick & Exuberant | 2, 1, 0 |
| 8 | X | I would describe "Dog Name's" coat as: | Dull, Fairly Shiny, Glossy | 2, 1, 0 |
| 9 | X | "Dog Name's" skin is dry & flaky: | Usually, Sometimes, Almost Never | 2, 1, 0 |
| 10 | X | I would describe poop scooping for "Dog Name" as: | A Nightmare, Less Than Ideal, Surprisingly Simple | 2, 1, 0 |
| 11 | X | "Do you choose for us to formulate your pet's diet without any of the following ingredients?" | Soy or corn, wheat or other grains | |

FIG. 8

| Priority | Age | Breed | Question # | Question Answer | Grain Free Selected | Kibble (Recommended) | Kibble (Alternate 1) | Kibble (Alternate 2) |
|---|---|---|---|---|---|---|---|---|
| 1 | - | - | 8 or 9 | 2 | Y | BGF3 | BGF2 | BGF1 |
| 2 | - | - | 10 | 2 | Y | BGF1 | BGF3 | BGF2 |
| 3 | - | - | 7 | 2 | Y | BGF3 | BGF2 | BGF1 |
| 4 | Senior | - | 7, 8, 9 or 10 | 1 | Y | BGF1 | BGF2 | BGF3 |
| 5 | Adult | Large Breed | 7, 8, 9 or 10 | 1 | Y | BGF1 | BGF2 | BGF3 |
| 6 | Adult | Medium | 8 or 9 | 1 | Y | BGF3 | BGF2 | BGF1 |
| 7 | Adult | Medium | 10 | 1 | Y | BGF2 | BGF1 | BGF3 |
| 8 | Adult | Medium | 7 | 1 | Y | BGF3 | BGF1 | BGF2 |
| 9 | Adult | Small | 5 | Ideal | Y | BGF1 | BGF2 | BGF3 |
| 10 | Adult | Small | 5 | Underweight | Y | BGF2 | BGF1 | BGF3 |
| 11 | Puppy | - | 7, 8 or 9 | 1 | Y | BGF2 | BGF3 | BGF1 |
| 12 | Puppy | - | 10 | 1 | Y | BGF2 | BGF1 | BGF3 |
| 13 | Senior | - | 7, 8, 9 or 10 | 0 | Y | BGF1 | BGF2 | BGF3 |
| 14 | Adult | - | 7, 8, 9 or 10 | 0 | Y | BGF1 | BGF2 | BGF3 |
| 15 | Puppy | - | 7, 8, 9 or 10 | 0 | Y | BGF2 | BGF1 | BGF3 |

FIG. 9

| Priority | Age | Breed | Question # | Question Answer | Grain Free Selected | Kibble (Recommended) | Kibble (Alt. 1) | Kibble (Alt. 2) |
|---|---|---|---|---|---|---|---|---|
| 1 | - | - | 5 | Underweight | N | C2 | C1 | C3 |
| 2 | - | - | 8 or 9 | 2 | N | B3 | B2 | B1 |
| 3 | - | - | 10 | 2 | N | B1 | B3 | B2 |
| 4 | - | - | 7 | 2 | N | A1 | A3 | A2 |
| 5 | - | - | 5 | Overweight | N | A1 | A2 | A3 |
| 6 | Senior | - | 8 or 9 | 1 | N | A3 | A2 | A1 |
| 7 | Senior | - | 10 | 1 | N | A1 | A2 | A3 |
| 8 | Senior | - | 7 | 1 | N | A3 | A2 | A1 |
| 9 | Adult | Large | 8 or 9 | 1 | N | A3 | A2 | A1 |
| 10 | Adult | Large | 10 | 1 | N | A1 | A2 | A3 |
| 11 | Adult | Large | 7 | 1 | N | A3 | A2 | A1 |
| 12 | Adult | Small | 8 or 9 | 1 | N | C3 | C2 | C1 |
| 13 | Adult | Small | 10 | 1 | N | C2 | C1 | C3 |
| 14 | Adult | Small | 7 | 1 | N | A1 | A3 | A2 |
| 15 | Adult | Medium | 8 or 9 | 1 | N | B3 | B2 | B1 |
| 16 | Adult | Medium | 10 | 1 | N | B2 | B1 | B3 |
| 17 | Adult | Medium | 7 | 1 | N | A1 | A3 | A2 |
| 18 | Puppy | - | 8 or 9 | 1 | N | C3 | C2 | C1 |
| 19 | Puppy | - | 10 | 1 | N | C1 | C2 | C3 |
| 20 | Puppy | - | 7 | 1 | N | A2 | A3 | A1 |
| 21 | Senior | - | 8, 9, 10 or 7 | 0 | N | A1 | A2 | A3 |
| 22 | Adult | Large | 8, 9, 10 or 7 | 0 | N | A1 | A2 | A3 |
| 23 | Adult | - | 5 | Overweight | N | A1 | A2 | A3 |
| 24 | Adult | Medium | 8, 9, 10 or 7 | 0 | N | B1 | B2 | B3 |
| 25 | Puppy | - | - | - | N | C2 | C1 | C1 |
| 26 | Adult | Small | 8, 9, 10 or 7 | 0 | N | C1 | C2 | C3 |
| 27 | - | - | 6 | Begrudgingly | N | C1 | C2 | C3 |

FIG. 10

SYSTEMS AND METHODS FOR ORDERING AND MANUFACTURING CUSTOM PET FOOD

FIELD

The present disclosure relates to systems and methods for ordering custom pet food, and in particular, systems and methods for collecting specific pet information and utilizing that information to create a custom food product.

BACKGROUND

The inventions disclosed relate generally to methods for ordering and manufacturing pet foods, and more particularly, to an algorithm and process for manufacturing a pet food customized to the health and nutrition requirements of an individual pet.

Due to economies of scale, retail pet food manufacturers typically manufacture their pet foods in large quantities and a limited number of formulations. Most manufacturers offer, for example, dog food in several flavors, and in a puppy formula, an adult dog formula, and a mature or inactive dog formula. Some manufacturers offer breed-specific or size-specific formulas. Some manufacturers offer more specialized formulas for dogs having specific food allergies or nutrient responsive diseases. Similarly, retail cat food is typically offered in limited variety of formulas of different flavors or for different stages of development. However, the range of pet food choices does not meet the highly variable preferences and dietary requirements of individual pets. For example, an individual pet may have specific dietary requirements because of an existing illness or disease, or because of a genetic predisposition towards a disease. In addition to nutritional requirements, pet owners and pets have preferences regarding the form, flavor, shape and texture of the food.

Accordingly, it would be desirable to provide a method of manufacturing a pet food for an individual pet that uses an algorithm that takes into account a variety of pet variables. In addition, it would be desirable to provide the pet owner with specific pet feeding and care information regarding their pet.

SUMMARY

In one aspect, the present invention provides a method for customizing a pet food for a pet, the method comprises obtaining a first pet profile information from a user, wherein the first pet profile information includes at least one of a species, an activity level, a medical history, a breed, a gender, a breeding status, a feeding method, an age, a spayed/neutered status, a snack schedule, a biological sample, a body condition, a dental health, a coat information, a digestive health information and a weight of the pet. The method also comprises obtaining a second pet profile information from a user, wherein the second pet profile information includes at least one of a preference regarding an ingredient, a food form, a flavor, a protein source, a shape and a texture; correlating the first pet profile information and second pet profile information to a stored nutritional information; and determining a pre-made pet blend based upon the correlation of the first pet profile information and the second pet profile information to the stored nutritional information.

In another aspect, the present invention provides a method for customizing pet food includes obtaining, at a user interface, information pertaining to pet attributes and preferences to form pet profile information, wherein the attributes include at least one of a species, an activity level, a medical history, a breed, a gender, a breeding status, a feeding method, an age, a spayed/neutered status, a snack schedule, a biological sample, a body condition, a dental health, a coat information, a digestive health information and a weight of the pet, and wherein the preferences include at least one of user or pet preferences regarding an ingredient, a food form, a flavor, a protein source, a shape and a texture; correlating the pet profile information with stored nutritional information to determine at least one wellness variable; determining a pet food formula based upon the at least one wellness variable; and manufacturing pet food according to the pet food formula.

In another aspect, the present invention provides a system for customizing pet food for a pet is also provided, which comprises a computer; a user interface coupled to the computer and configured to prompt a user at the user interface to enter information regarding a pet information of the pet. The computer is configured to receive the pet information from the user. The pet information includes at least three of a species, an activity level, a medical history, a breed, a gender, a breeding status, a feeding method, an age, a spayed/neutered status, a snack schedule, a biological sample, a body condition, a dental health, a coat information, a digestive health information and a weight of the pet. The system also comprises a processor coupled to the computer and configured to correlate the pet information with one or more wellness variables to form a pet food formula recommendation. The system also includes an ordering device configured to utilize the pet food formula recommendation to facilitate fulfillment of a pet food order.

BRIEF DESCRIPTION OF THE DRAWINGS

FIG. 6 illustrates a priority listing of wellness variables in accordance with an embodiment of the invention.

FIG. 7 illustrates a chart of kibble identifiers in accordance with an embodiment of the invention.

FIG. 8 illustrates a chart of questions and inputs in accordance with an embodiment of the invention.

FIG. 9 illustrates a chart of prioritizations and kibble recommendations in accordance with an embodiment of the invention.

FIG. 10 illustrates a chart of prioritizations and kibble recommendations in accordance with an embodiment of the invention.

DETAILED DESCRIPTION

Exemplary embodiments of apparatus and methods for customizing pet products are described below. The systems and methods facilitate the manufacture of a customized product that is directed to the specific needs of an individual pet. As used hereinafter, pet product includes pet foods as well as pet food components. Although the pet products may include food components that are manufactured in bulk, i.e., pre-made, the pre-made components are combined with custom made products to produce an end product that is customized to the particular needs of an individual pet. Thus, the phrase customized product includes products that have no pre-made food components as well as products that include pre-made food components and custom made additives. In addition, although the method is often described in terms of a complete process, it should be understood that any portion of the process can be used separately or in combination with any other portion of the process described hereinafter.

It should also be understood that, to the extent the present application is directed to the methods as described below in more detail, such methods should not be limited to a particular food manufacturing apparatus. It should be further understood that the methods described herein can be implemented in a variety of ways, including the use of software which runs on one or more computers that controls the manufacturing of the pet food.

Figure 1:
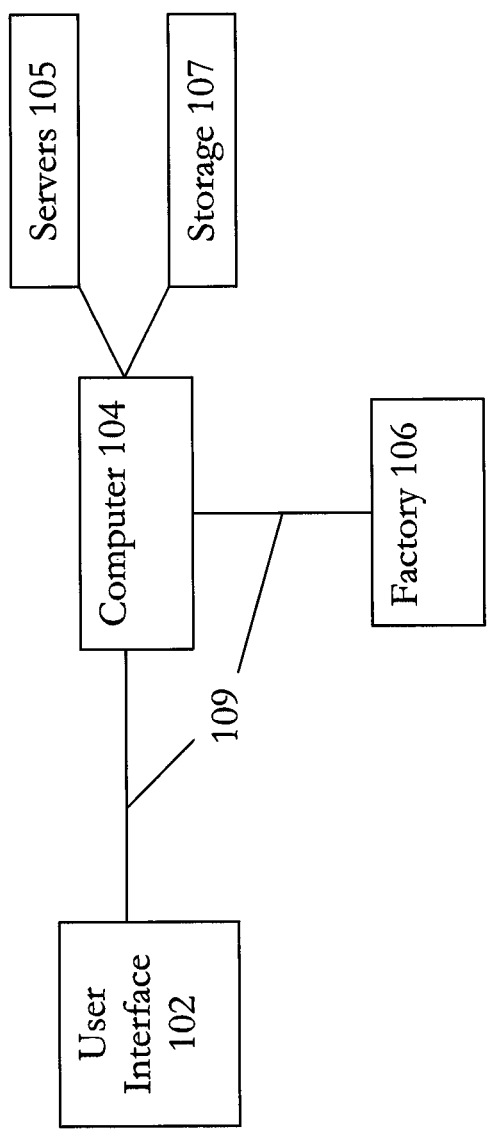
FIG. 1 is a schematic illustration of an apparatus for manufacturing a customized pet food.

FIG. 1 is a schematic illustration of an embodiment for a system for manufacturing a customized pet food. The system includes an electronic user interface 102 and a computer 104 which is electronically coupled to user interface 102. The system also includes a factory 106 coupled to computer 104.

More specifically, user interface 102 and/or factory 106 may be either remote from, or local to computer 104, and includes a data entry system such as a desktop computer, or an input device such as a keyboard, touch screen, mouse, or card reader, and an output device such as a monitor. In another embodiment, user interface 102 is a voice-activated telephone system. User interface 102 may be coupled to computer 104 through standard computer cables, a phone line or a dedicated computer network cable, which transmits the user input to computer 104 for processing, a wireless communications link, a cellular communications link, and/or the like. For example, a user such as a consumer may connect to computer 104 via a computer network such as the Internet, through, for example, a wireless connection. Alternatively, the user may use a user interface local relative to computer 104, both computer 104 and user interface 102 located, for example, in a retail grocery store. User interface 102 can comprise Internet Explorer (such as, for example, IE 7.0), Mozilla FireFox, Safari and/or the like, In addition, user interface 102 can use Macromedia Flash and/or other functionalities.

As used herein, the term "user" may be used to refer to any type of individual consumer, customer, researcher and/or or the like that receives and/or transmits information from/to user interface 102. Users include, but are not limited to, pet owners, veterinarians, manufacturers, organizations, wholesalers, vendors, members and/or the like.

Computer 104 may be, for example, a typical, commercially available personal computer with networking capability, including, but not limited to a personal computer, mobile device, tablet, iPad, laptop, and/or the like. In addition and/or in another embodiment, computer 104 may comprise more computers 104, servers 105, and/or storage 107 connected directly and/or through a network 109.

Servers 105 can comprise one or more servers and any hardware and/or software suitably configured to facilitate communications between the various system components as discussed herein. Servers 105 can operate as a single entity in a single geographic location or as separate computing components located together or in separate geographic locations. Information received and/or processed at servers 105 may pass through a firewall prior to being received and processed. As used herein, "transmit" may include sending electronic data from one system component to another over a network connection. Additionally, as used herein, "data" may include encompassing information such as commands, queries, files, data for storage, and the like in digital or any other form. Servers 105 may provide a suitable web site or other Internet-based graphical user interface elements accessible users. In one embodiment, servers 105 may use software such as Linux Kernel, Apache, MySQL and/or PHP. Servers 105 may comprise the Microsoft Internet Information Server (IIS), Microsoft Transaction Server (MTS), and Microsoft SQL Server, or the like. In addition servers 105 may be used in conjunction with the Microsoft operating system, Microsoft NT web server software, a Microsoft SQL Server database system, and/or a Microsoft Commerce Server. Additionally, components such as Access or Microsoft SQL Server, ORACLE, SYBASE, InterBase, etc., may be used to provide an Active Data Object (ADO) compliant database management system.

Storage 107 comprises one or more devices and/or software systems for storing data in analog or digital format. Storage 107 includes, but is not limited to, magnetic tape, flash drives, RAM, hard drives, databases, optical storage devices, zip drives, and the like. The databases used herein can comprise one or more local, remote or other databases used for information storage and retrieval. The databases can be a graphical, hierarchical, relational, and/or object-oriented database.

Network 109 comprises any electronic communications means which incorporates both hardware and software components of such. Network 109 can comprise any suitable communication channels, such as, for example, a telephone network (such as a public switched telephone network or Integrated Services Digital Network (ISDN)), an extranet, an intranet, Internet, point-of-interaction device (personal digital assistant, cellular phone, kiosk, etc.), online communications, off-line communications, wireless communications, transponder communications, local area network (LAN), wide area network (WAN), networked and/or linked devices and/or the like. Moreover, network 109 may also implement TCP/IP communications protocols, IPX, Appletalk, IP-6, NetBIOS, OSI and/or any number of existing and/or future protocols. If network 109 is in the nature of a public network, such as the Internet, various encryption and security protocols may be used to secure network 109, including, but not limited to SSL encryption and "Blowfish." Specific information related to the protocols, standards, and application software utilized in connection with the Internet is generally known to those skilled in the art and, as such, need not be detailed herein.

Communication between computer 104, servers 105, user interface 102, factory 106, storage 107 and/or network 109 may be facilitated using additional software and/or hardware (not shown) software. For instance, any type of software and/or hardware to facilitate communication and data storage within computer 104 and/or factory 106. For example, software and/or hardware can comprise one and/or more of the following: a host server and/or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. As those skilled in the art will appreciate, software and/or hardware can include an operating system (e.g., MVS, Windows NT, 95/98/2000/XP, OS2, UNIX, MVS, TPF, Linux, Solaris, MacOS, AIX, etc.) as well as various conventional support software and drivers typically associated with computers.

Computer 104 provides an electronic input to user interface 102, which input prompts a user at user interface 102 to answer a series of questions to form an pet profile of the pet. In one embodiment, for example, computer 104 is a computer network server such as a web server which supports a web "page" written in Hyper-text Mark-up Language (HTML), virtual reality mark-up language (VRML), handheld device mark-up language (HDML), standard generalized mark-up language (SGML), dynamic HTML, or the like or a web site including multiple such "pages". The web page or web site is the electronic input to the user interface 102, and the user can click on radio buttons on the web pages to answer questions regarding the pet profile. In one embodiment, the user enters the answers using an input device such as a mouse, touch screen or keyboard. In one embodiment, a user may provide a text entry answer. In another embodiment, the user may select an answer from a drop-down menu, slider bar or by clicking on a button. It should be recognized however that the user input and methods disclosed herein are not limited to practice through electronic user interfaces and electronic control systems. For example, the user input may be obtained by administering a written or verbal questionnaire to a user or customer to form the pet profile.

The electronic input from computer 104 to user interface 102 includes, but is not limited to, questions regarding a pet's species, age, weight, gender, breed, activity level, breeding status, eating style, digestive health, skin and coat health, dental health, muscle and joint health, medical history, genetic information, current health status, and the like. In addition, the electronic input can include, for example, the preferences of the pet, or the pet's owner, regarding ingredients, food form, flavor, protein source, shape and texture. For example, in one embodiment, the pet owner can indicate a preference towards a grain free pet food blend. In another embodiment, the pet owner can indicate a preference towards a vegan or vegetarian pet food blend. The user may also be prompted to provide the time of year and/or date or computer 104 may provide the time of year and/or date according to an internal clock. Together this information forms the pet profile information. In one embodiment, the user is a consumer such as a pet owner. In an alternative method, the user is a pet care provider such as a veterinarian or veterinary technician who administers a written questionnaire to the pet owner, and then enters the data into user interface 102, or directly into computer 104.

In one embodiment, computer 104 receives and processes the pet profile information contained and generates signals which are communicated to factory 106. In one embodiment, computer 104, servers 105 and/or storage 107 can process the pet profile information by combining it with stored nutritional information to generate a customized pet food recommendation. The stored nutritional information may include, but is not limited to, information that correlates certain nutrients with certain pet attributes, caloric information, nutritional information, and the like. As used herein, a customized pet food recommendation can include a pre-made blend, one or more additives, a newly devised pet food formula and/or the like.

Generally, factory 106 is programmed to receive one or more input signals from computer 104. The input signals from computer 104 represents the customized pet food formula created according to the pet profile of the pet and stored nutritional information. In an alternative embodiment, the input signal from computer 104 represents the customized pet food formula created according to the pet profile of the pet in combination with a biological sample analysis and/or nutritional data stored in a database. In one embodiment, the input signals represent a set of manufacturing instructions to factory 106.

As used herein, factory 106 is a remote and/or local computer, ordering device, facility, network of computers, and/or the like for facilitating fulfillment of a pet food order and/or for manufacturing pet food. For example, in one embodiment, factory 106 is similar to the manufacturing apparatus described in U.S. Pat. No. 6,493,641, entitled "Methods and Apparatus for Customizing Pet Food," and U.S. Pat. No. 6,576,280, entitled "Systems for Customizing Pet Food," the contents of both which are incorporated herein in their entireties. In another embodiment, factory 106 is an ordering device that facilitates the fulfillment of user pet food orders. Communications to factory 106 are made through any of the communications methods described herein.

It should be understood that, to the extent the present application is directed to the methods as described below in more detail, such methods should not be limited to a particular food manufacturing apparatus. It should be further understood that the methods described herein can be implemented in a variety of ways, including the use of software which runs on computer 104 and controls the real-time manufacturing of the pet food. In addition, it should be understood that the user input can occur through any means, electronic or otherwise and the processing can occur through any means, electronic or otherwise. For example, the methods described below, may be practiced by administering a written or verbal questionnaire to a user or customer to form the pet profile, using the pet profile to generate a customized pet food formula, and/or manufacturing the customized pet food with manual control of the operation of factory 106. In addition, the methods need not occur in any particular order, and need not include all of the exemplary steps provided.

Figure 2:
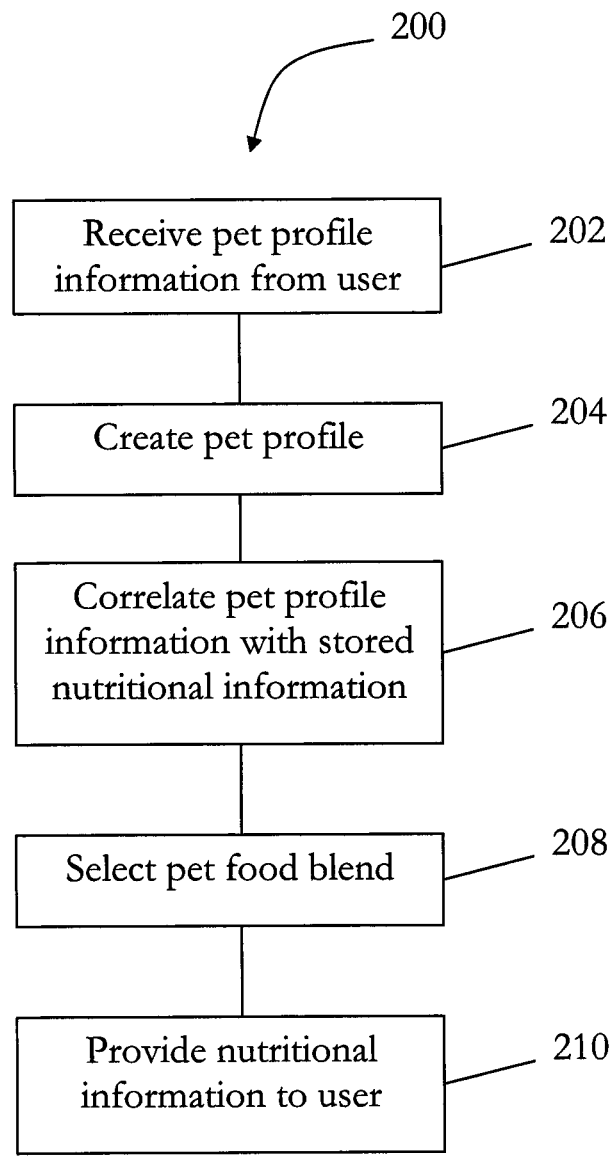
FIG. 2 is a flow chart illustrating a method for manufacturing a customized pet food in accordance with one embodiment of the invention.

For example, with reference to an exemplary embodiment of a method 200 illustrated in FIG. 2, a user such as a consumer connects to user interface 102 via a computer network such as the Internet, from a home computer connected to a home phone line. Computer 104 provides an electronic input to user interface 102, which input prompts a user at user interface 102 to answer a series of questions to form the pet information of the pet. The answers from the user are communicated electronically to computer 104 (step 202), and computer 104 processes the information contained in the answers to create a pet profile (step 204).

The pet profile is composed of answers to questions pertaining to, but not limited to, a pet's name, species, age, weight, gender, breed, spayed/neutered, activity level, breeding status, digestive health, medical history and genetic information, current health status, body condition, feeding method, snack schedule and flavor preferences. In addition, the pet profile includes indications regarding, for example, the preferences of the pet, or the pet's owner, regarding form, protein source, flavor, shape and texture. Further, the pet profile also includes information regarding the season, date or time of year. The information for the season and the time of year may either be obtained through questions asked to the user, or through an internal clock on computer 104. In one embodiment, the pet profile also includes genetic and or biological information about the pet. In one embodiment, the user is a consumer such as a pet owner. In an alternative embodiment, the user is a pet care provider such as a veterinarian or veterinary technician who administers a written questionnaire to the pet owner, and then enters the data into user interface 102, or directly into computer 104.

In addition to the pet profile created based on user input, the user may be also requested to input information obtained from a biological sample of the pet. The computer 104 utilizes information obtained from the biological sample analysis to obtain additional information regarding the pet. The information regarding the biological sample analysis can be obtained by any means and is not limited to electronic means. In an exemplary embodiment, the additional information regarding the biological sample analysis is pertinent to determining the pet's individual ability to react to specific dietary nutrients or ingredients and thereby change the health status of the pet (including, but not limited to stool quality, immune status, oral/dental health, skeletal health, skin and coat condition). In one embodiment, the analysis of the biological sample is obtained at the same time the pet profile information is obtained. In an alternative embodiment, the analysis of the biological sample is obtained after the pet has eaten the customized pet food. The analysis provides information that enhances the pet profile information and is used to modify and refine the customized pet food product by suggesting a different pre-manufactured kibble, adding specific additive ingredients, removing specific additive ingredients, and/or changing the amount of any included additive ingredient from the pet product formulation to enable the new formulation to better meet the needs of the pet. In one embodiment, the additional nutritional and biological analyses information is conveyed to the pet's veterinarian to recommend potential therapeutic components to the diet or a therapeutic treatment if appropriate. In an alternative embodiment, the veterinarian conveys the nutritional and biological analyses information to a pet food manufacturer. In the exemplary embodiment, the biological sample includes, but is not limited to, at least one of stool, urine, hair, blood, saliva, tissue, and DNA.

The biological sample analysis may help determine a pet's individual reaction to a diet and the pet's ability to change its health status, including, but not limited to stool quality, immune status, oral/dental health, skeletal health, skin and coat health. The pet's individual reaction and ability to change may be different than a reaction of another pet in the same category to the same diet. For example, in creating pet foods for the "average" dog, digestion tests are typically conducted on a statistically large group of animals and their reactions averaged. The predictions are made on how these diets may fare for other similar dogs. Individual variations are thus excluded during creating foods for the "average" pet.

Computer 104 correlates the pet profile information to nutritional information stored in one or more databases (step 206). The stored nutritional information, may include, for example, nutritional and other health benefits relating to vitamins, minerals, extracts and/or other nutrients. Based upon the correlation by computer 104, a pre-manufactured pet kibble or blend is then selected (step 208). In one embodiment, the custom pet food product includes a pre-manufactured kibble and a custom pet food additive. Computer 204 suggests a pre-manufactured kibble or blend from a number of possible pre-manufactured kibbles or blends and creates a pet food additive based on the pet food product formulation specific to the pet and in accordance with the pet profile of the pet. In an alternative embodiment, the pet food product includes a pre-manufactured kibble or blend and a pre-manufactured additive, such as a topping or sauce. The computer suggests a particular pre-manufactured kibble or blend from a number of possible pre-manufactured kibbles or blends and suggests a particular pre-manufactured topping from a number of possible pre-manufactured toppings. As used herein, the terms kibbles, blends, and clusters refer to formulations of pet foods. These formulations may comprise different ingredients and be formed into different shapes and/or sizes. As used herein, the terms "topping", sauce, gravy, thickener, powder, and coating refer to an additive or additives to a pet food product that can be added by either the manufacturer or end user. Such toppings may include, but are not limited to, fruits or fruit extracts, vegetables or vegetable abstracts, grains, proteins, fiber and/or the like. The toppings may be in solid and/or liquid form.

Alternatively, based upon the correlation by computer 104, computer 104 sends information to factory 106, which in turn can manufacture a specific blend of pet food and/or carry out an order for a specific blend of pet food. For example, computer 104 can combine the stored nutritional information with the pet profile to create a customized pet food formula specific to the individual pet which is also stored in the database. Computer 104 can then generate signals for factory 106 to manufacture food according to the customized pet food formula.

In one embodiment, the user can then view nutritional information related to the selected blend (step 210). For example, computer 104 can be programmed to assemble the pet profile and nutritional data into printed material. In an exemplary embodiment, the printed material includes customized pet feeding and care information for the individual pet, along with an ingredient statement, guaranteed analysis of the pet food, and a product label. In alternative embodiments, the printed material may also include recommendations regarding the use of treats and supplements, exercise of the pet, and veterinary care.

In one embodiment, the user may change the food blend and/or make additions to the food blend based upon the provided nutritional information. Based upon the user input (or lack thereof), a final pet food product is selected. This final pet food product can comprise a pre-made blend, a modified pre-made blend, a newly manufactured blend and/or nutritional "toppings."

In one embodiment, the customized pet product includes a first basal portion common to many types of finished food products and also includes a second supplemental portion that incorporates additional ingredients. The additional ingredients, in one embodiment, are in the form of a sauce, a coating, a gravy, a solution, a topping, and a powder. In alternative embodiments, the additional ingredients can take other forms. The two-portion food provides a large variety of customized foods while keeping the inventory of basal ingredients and supplemental ingredients to a minimum. Only a minimal number of ingredients are utilized since a minimum number of nutrient bases (for the major categories of pet foods) can be used in conjunction with micro ingredients such as vitamins, minerals, fats, antioxidants, flavors, soluble fibers, and other functional ingredients to provide a large variety of complete, customized pet foods that address a pet's specific nutritional and other needs.

In an exemplary embodiment, the basal food portion is pre-made into kibbles and an additive is custom blended according to each pet's specific pet profile, biological sample analysis, and/or the correlation made by computer 104. A set of pet nutrient profiles, with the exception of fat, soluble fiber, and vitamin E, is created to satisfy the macronutrient needs of different dogs. For example, a set of 10 profiles is utilized to create 10 formulas, e.g., F1 through F10. These formulas are utilized to manufacture, according to known extrusion methods, pre-made kibbles which are packaged into packages, such as bags.

Next, an additive formulation, such as a sauce, is formulated in a number of varieties, e.g., S1 through S25, which provide the required amounts of fat, fiber, and vitamin E. The additive formulations are created to make each of the bases F1 through F10 complete and balanced when mixed with an appropriate additive in an appropriate amount. Additives S1 through S25 are made in any of the consumer preferred flavors and with inclusions of other desired micronutrients. Thus, the total number of additives increases by a factor such as four.

For example, additive S3 (at 12.5% of total) is combined with formula F5 (at 87.5% of total) to create a complete and balanced food that provides all the nutrient needs of a specific pet. Additive S3 is, for example, a sauce having a salmon flavor and other desired micronutrients, such as extra vitamin E, for a stressed pet. Multiple additives can be formulated to be compatible with multiple pre-made bases.

In one embodiment, the pre-made bases, F1 through F10, are packaged in bags and brought to a store. Components, such as flavors, micro-nutrients, fats, soluble fiber, and preservatives, to make the additives S1 through S25 are also brought to the same store in containers, such as dispensing bottles. As a customer's requirements are determined, a specific base, such as F3, is selected and an additive formulation, say F5, in a customer chosen flavor, say tuna flavor, is created on site. Using the dispensing bottles, the additive is mixed in a bottle, sealed, and given to the consumer with proper mixing and feeding instructions. The user combines the kibbles with the additive to provide a customized pet food to the pet. In one embodiment, the additive is one of a sauce, a powder, a coating, a thickener, a topping and a gravy. In alternative embodiments, the additive is a combination of two or more of the above listed additives.

The additives are formulated such that when the additives are combined with the kibbles, a complete, balanced and customized nutritious product is supplied. In one embodiment, the additives are manufactured by an operator in accordance with information obtained from the pet's pet profile.

The ratio of additives to kibbles is a factor in supplying a complete and nutritious food to pets. The macronutrients in a pet food (such as the protein, carbohydrates, fat and moisture) are provided to a large extent by the base kibbles. However, the caloric and fat content of the combined food can be adjusted by manipulating the fat content of the additives. Thus, for an additive added at 12.5% of the total pet food (base plus additive), the fat content of the additive is varied between 15% and 70%. This variation allows addition of between 2% and 11% fat, and selecting the appropriate level of fat in the additive allows fat levels of the combined pet food to vary between about 4% and 20% which is a typical range for pet foods.

Pets need the vitamins and minerals that make up a complete and balanced diet. These vitamins and minerals are usually sourced as premixes from vitamin suppliers and are added at typically less than 1% of the formulation. In one embodiment, these vitamins and minerals are added to the kibbles. In an alternative embodiment, for vitamins and minerals that need to be protected from high thermal processing such as extrusions, the vitamins and minerals are added to the additives instead. Higher dosages of vitamins such as Vitamin E and Vitamin C are suggested for individual dogs that are senior, active, or undergoing immune deficiency. Higher than basic levels of these vitamins can be delivered through addition of vitamins in the additives, typically at low levels such as from 0 to 0.5%.

In addition, if a pet needs additional levels of soluble or insoluble fiber, the fiber is delivered through the additives in amounts typically ranging between 0.1% and 1.0% of the total formulation, or between 0.5% and 20% of the sauce depending upon the sauce to the base kibble ratio.

Palatable coatings such as animal digests, typically used in pet food formulations, can be used to make the sauce highly palatable to the pets. These coating levels can be varied (0.5% to 10%) to compensate for the varying palatability effect of other ingredients such as fat levels. Thus, even low-calorie pet foods can be made as palatable as high-calorie foods by adding an extra amount of palatable coatings to the kibbles in a low-calorie diet.

Other specialized micronutrients, as they are discovered for their effect in pet nutrition can also be delivered through the additives as a delivery mechanism. For example, fish oil as a source of omega three fatty acids for healthy skin and coat, is included in the additives in the required quantities (such as between 0 and 5%). Alternatively, sodium acid pyrophosphate for dental and skeletal health is included in the additives in the required quantities (such as between 0 and 5%).

In addition, and in one embodiment, the additives are visually appealing and functionally stable. For example, pH lowering agents (such as phosphoric acid or sodium bisulfate and/or Sorbic acid) are added at between 1.0% and 5.0% to bring the pH to between 2.0 and 3.0 to provide a resistance to bacterial, fungal or other microbial spoilage to the additives. Additive stabilizers, for example for a sauce, such as gums or fibers are, in one embodiment, added at between 0.5% and 2.0% to make the additive components well integrated. Other flavors and colors are added at 0 to 3.0% to provide the desired flavor and color of the additive to the customer. For a sauce additive, it has been determined that adding Psyllium fiber at between 0 and 1.0% of the sauce amount binds water and prevents separation of aqueous and fat phases in the sauce.

In an alternative embodiment, the kibbles are not pre-manufactured but instead the basal food portion is pre-mixed and transported to specific locations, such as retail locations. Ingredients to make the supplemental portion are kept at each retail location. Manufacturing apparatus at each specific location are utilized to blend the appropriate supplemental ingredients with the pre-made basal portion and form a manufactured food. Thus the manufacturing process is simplified and can be diffused to many locations instead of one or a few central locations.

Figure 3:
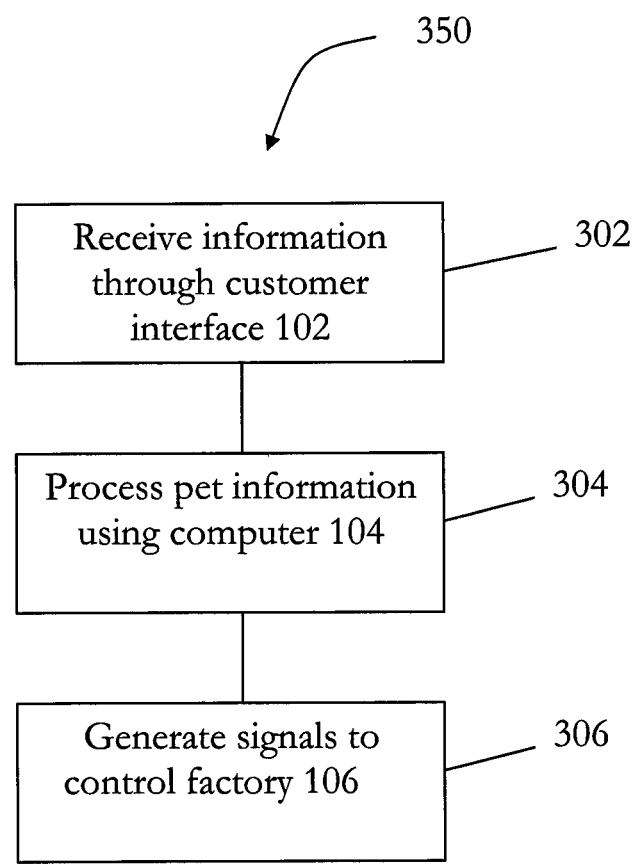
FIG. 3 is a flow chart illustrating a method for manufacturing a customized pet food in accordance with one embodiment of the invention.

FIG. 3 is a flow chart illustrating a method 350 for manufacturing a custom pet food. In one embodiment, method 350 generally includes obtaining user input through electronic user interface 102 (step 302), processing the input with stored data on computer 104 (step 304), and generating signals to control the operation of a factory 106 (step 306).

To manufacture a food in accordance with the above method, the created pet food formulation is utilized by computer 104 to direct factory 106 regarding the proper ingredients to add and the proper amounts of each added ingredient and/or to indicate to factory 106 which pre-made pet food blend should be selected for the user.

In one embodiment, computer 104 is used to create and print a label that identifies the individual pet for which the food was manufactured, and lists the product formula, a list of nutritional benefits or claims, an ingredient list, a date of manufacture, and the like. In an alternative embodiment, computer 104 is further coupled to a digital camera which captures an electronic image of the individual pet, and transmits the image to computer 104 to generate a photo label of the pet for the food package, which is printed by printer on a label as described above. A printer may also be used to produce printed material such as a pamphlet or flyer having pet care information and instructions including, for example, a description of the customized pet food formula, feeding recommendations including specific recommendations regarding amount and feeding methods, recommendations for treats and supplements, and recommendations on veterinary care.

Figure 4:
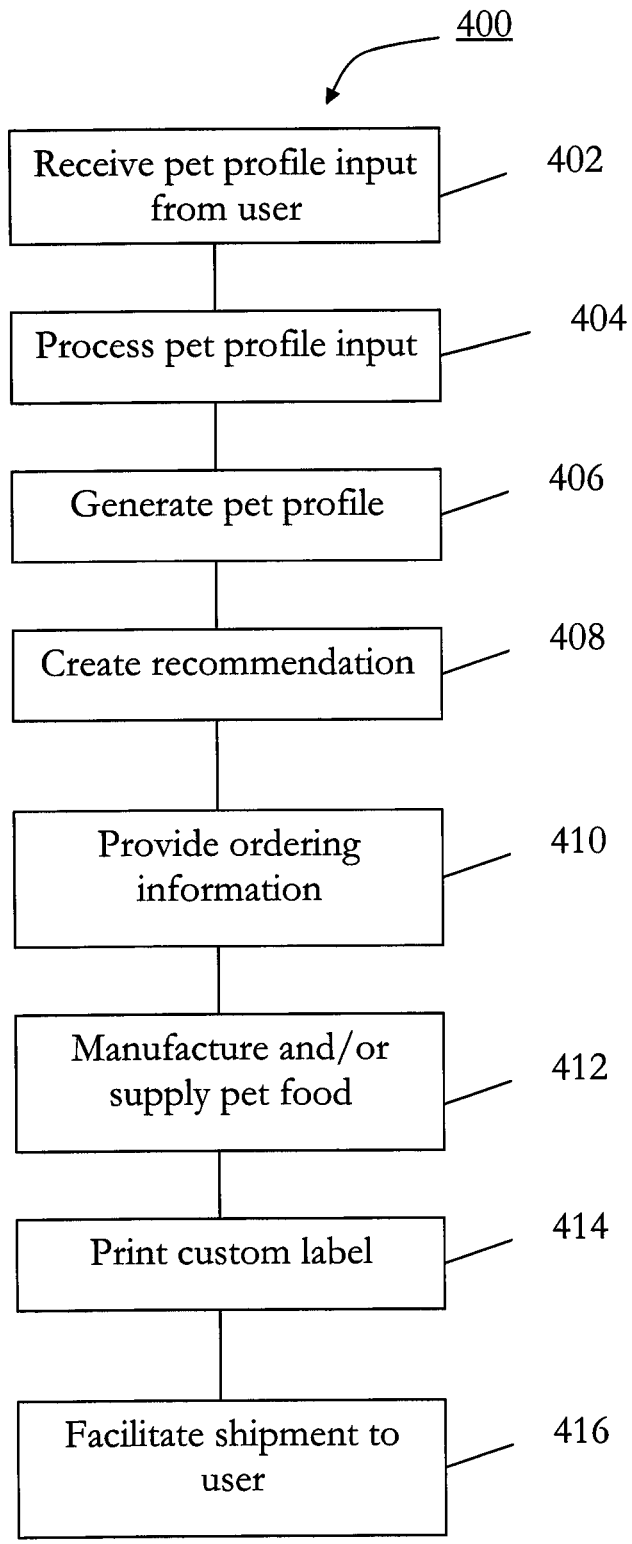
FIG. 4 is a flow chart illustrating a method for producing a customized pet product in accordance with an embodiment of the invention.

FIG. 4 illustrates a method 400 of obtaining a customized pet food product. In an exemplary embodiment, a pet owner (consumer) that is a purchaser of a customized pet food product supplies pet profile and/or a biological sample (i.e., stool sample) using user input 102 and/or any other means. In one embodiment, the consumer supplies a completed questionnaire and/or biological via the Internet, in the mail or in person. This information is then received by computer 104 (step 402).

In one embodiment, analytical data is obtained from the biological sample by a veterinarian/technician located on site. In an alternative embodiment, the sample is sent to a central lab for analysis. The analysis is performed on the biological sample with respect to examining several health and digestive indicators. Data from the biological sample analysis is combined with the pet profile information and entered into a system including a pet food product customization model. Alternatively, the pet profile information is used without any biological sample.

Computer 104 processes the pet profile information and/or biological sample (step 404) utilizing at least one algorithm and generates a pet profile (step 406). Each profile may have a unique identifying code and contains the specific customized food product and feeding instructions recommended for the specific pet. The recommended food product includes a pre-manufactured kibble and a customized additive. In one embodiment, the pre-manufactured kibble is selected from a variety of pre-manufactured kibbles and the additive is a liquid additive that is made on site, typically in the presence of the consumer.

For example, with reference to an exemplary embodiment illustrated in FIG. 7, there are four base pre-made kibble types: A, B, BGF (type B, grain free), and C. Each base kibble can comprise a different source of protein, for example, chicken, lamb, salmon or the like. Thus, in the illustrated embodiment, base kibble type A can come in chicken (type A1), lamb (type A2), or salmon (type A3). As such, there are twelve different pre-made kibbles that can be selected.

Computer 104 then provides information to user interface 102 regarding the particular customized pet food, pre-made kibble best suited for the pet and/or customized additive formula that has been created based upon the individual pet's profile (step 408). For example, in one embodiment, computer 104 provides the user with information regarding a pre-made kibble A2 that is formulated to meet the nutritional needs of the pet based on the information in the pet profile and stored nutritional information. Alternatively, the system indicates a recommendation for the pet to see a veterinarian prior to buying a customized food, if certain "warning" signs are present in the profile. This recommendation provides the consumer with added health information about the pet between regular vet visits.

Computer 104 provides user with ordering information (step 410) on how to obtain a bag of the recommended pet food product. By providing the user with ordering information, computer 104 can communicate information through user interface 102 regarding pet food size, quantity, cost and/or the like. In one embodiment, computer 104 provides an option through user interface 102 to set up an automatic standing order. For example, the user can select to receive a 2-pound bag of pet food monthly. In another embodiment, computer 104 provides the user with an option to automatically update the user's pet food order based upon the age of the pet. For example, the user may receive a 2-pound bag of a certain formulation of pet food monthly for 6 months, and then every six months, the formulation will automatically change in response to the aging of the pet.

In another embodiment, computer 104 sends a message to a user, through user interface 102, telephonic means, electronic means, or the like, which provides the user with additional questions in order to update a previously stored pet profile. For example, after the user answers an initial questionnaire, computer 104 can send an email to the user (for example, every month, semi-annually, annually, or the like), requesting additional information from the user regarding the pet's health. In one embodiment, the user selects to receive update emails annually. While the example references use of an email, any other communication means may be used. In addition, the email may contain links to user interface 102 and/or the like.

In one embodiment, computer 104 communicates with factory 106 to make and/or supply the custom pet food and/or pre-made food and/or food additive, utilizing the recommended formulation (step 412). In addition, customized feeding instructions and package labels are printed (step 414). The label may include personalized pet information, nutritional information and/or claims, feeding information, information about the recommended frequency and conditions of future biological sample analyses, and/or information about the recommended frequency of profile updates for their pet. The computer 104 then facilitates shipping the customized pet food product to the consumer (step 416).

For a repeat purchase, a consumer returns to user interface 102 and provides their pet's unique code to access their pet's profile. They may update/change the profile information and/or provide a new biological sample, either of which could result in a difference in the recommended food. Alternatively, the consumer leaves the profile as it is and replenishes their pet's current food supply.

Alternatively, a customized additive is ordered by at least one of mail, catalogue, and the Internet, and is shipped directly to the consumer's home. Then, only the pre-made bases are purchased at a retail outlet. Once the consumer receives a base formula recommendation, the consumer purchases the base wherever convenient, and the additive is shipped directly to the consumer in finished or almost finished form. In one embodiment, the consumer adds one of water and oil to the shipped sauce. In alternative embodiments, the sauce is produced either on site or off site and the production is either manual or automated.

Figure 5:
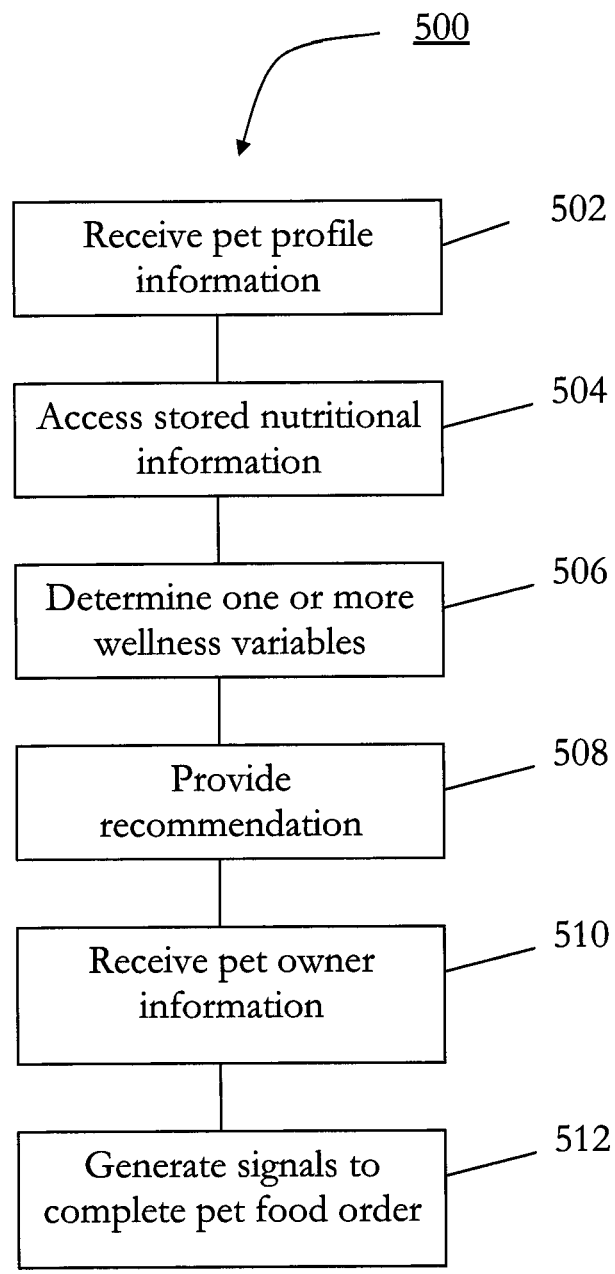
FIG. 5 is a flow chart illustrating a method for determining a customized pet product in accordance with an embodiment of the invention.

In one exemplary embodiment of a determination method 500 illustrated in FIG. 5, computer 104, servers 105 and/or storage 107 are configured to determine a pet food product based upon the pet profile information, biological sample and/or stored nutritional, health and other information. Computer 104 receives pet profile information (step 502). For example, with reference to an exemplary embodiment illustrated in FIG. 8, the pet profile information can include, but is not limited to, answers to questions about the pet's gender, age, breed, activity level, weight, eating habits, joint health, coat health, skin health, digestive health and the like. The pet profile information can also include answers to questions about the pet owner's food preferences, for example, whether the owner prefers a grain-free diet for the pet, a soy-free diet for the pet, a corn-free diet for the pet, the source of primary protein for the pet (i.e., chicken, lamb, beef, or fish), and the like.

Computer 104 then accesses stored nutritional information (step 504). In one embodiment, and with further reference to FIG. 8, computer 104 assigns a weight to one or more answers to the questions about the pet or pet owner preferences. For example, with respect to a question about the pet's coat, computer 104 may weight a response of "dull" higher than a response of "glossy."

Computer 104 then determines one or more wellness variables (step 506), based on the pet profile information and stored nutritional information. In one embodiment, computer 104 uses the weight of the responses to help determine one or more wellness variables. As used herein, "wellness variables" refers to one or more nutritional claims that the formulas in each pet food formulation support. For example, the nutritional claims may include, but are not limited to DHA from omega-rich fish oil to help nourish brain and vision development; calcium, phosphorus and other minerals to help build strong teeth and bones; EPA, an omega-3 fatty acid, and glucosamine to support joint health and mobility; hard kibble texture to help reduce plaque build-up on teeth; optimal protein and fat levels to help the pet maintain healthy weight and ideal body condition; high-quality sources of carbohydrates for sustained energy; omega-6 fatty acids and zinc to help nourish skin and promote a healthy coat; easily digestible formula that is gentle on the digestive system; alternative sources of carbohydrates—formulated without grain or soy and/or the like.

A particular fed food formulation may support numerous nutritional claims, or it may be directed to only one nutritional claim. For formulations that support numerous nutritional claims, the nutritional claims may be prioritized based upon a variety of factors, including but not limited to the breed information, the pet age information, the pet weight information, the pet activity level, the pet's digestive health, the pet's eating habits, the pet's joint health, the pet's coat or skin information, the pet owner's pet food preferences, and the like. For example, in one embodiment, the wellness variables for a particular pet food formulation are prioritized based on the pet's age, the pet's breed, and the pet's coat health. In another embodiment, the wellness variables for a particular pet food formulation are prioritized based on the pet's weight, the pet's age and the pet's digestive health. While these two embodiments exemplify two types of prioritization, the wellness variables can be prioritized based on any pet profile information, pet owner preference information, nutritional information and/or the like.

For example, one embodiment of wellness variable prioritization 600 is illustrated in FIG. 6. In this embodiment, pet food cluster type A is formulated such that the most prioritized nutritional benefit it provides is optimal protein and fat levels to help pets maintain healthy weight and ideal body condition, while an easily digestible formulation is a lesser-prioritized benefit. In contrast, pet food cluster type B is formulated such that one of the most prioritized nutritional benefits it provides is an easily digestible formulation, while optimal protein and fat levels are a lesser-prioritized benefit. As such, for pets that need optimal protein and fat to fulfill their health needs, computer 104 would select pet food cluster type A. In another embodiment, each pet food cluster can be formulated using a different protein source. For example, pet food cluster type A can comprise chicken, lamb or salmon.

In one embodiment, FIG. 9 and FIG. 10 illustrate kibble recommendations based upon the answers to the pet profile information received by computer 104. The kibble recommendations are based upon the pet profile information, pet or user preferences, stored nutritional information related to the kibble formulation, one or more wellness variables, one or more wellness variable prioritizations, and/or the like.

For example, in one embodiment, and with further reference to the embodiments illustrated in FIG. 5 and FIG. 9, pet profile information indicates that the pet is a puppy golden retriever and that the pet owner prefers a grain-free pet formula. Computer 104 uses this pet profile information and cross-references it with stored nutritional information and requirements related to golden retriever breeds and puppies, as well as stored nutritional information related to its grain-free formulations. Based upon this stored nutritional information, computer 104 then determines that the golden retriever would benefit from a custom formulation that is a grain-free formulation that has high-quality sources of carbohydrates for sustained energy, omega-6 fatty acids and zinc to help nourish skin and promote a healthy coat; and DHA from omega-rich fish oil to help nourish brain and vision development. Computer 104 determines that the recommended formulation is a cluster BGF type formulation, comprising lamb (BGF2) and provides this recommendation to the pet owner (step 508). The pet owner can select this recommendation, or modify the cluster type, protein type (i.e., change from lamb to salmon), and/or add any number of toppings (for example, a calcium-rich topping for the puppy's bone health). Computer 104 receives the owner's selection, modification and/or addition (step 510).

Computer 104 then generates signals to factory 106 according to the customized pet food formula in order to complete the pet food order (step 512). By generating signals to factory 106, computer 104 can signal to factory 106 to begin manufacturing the pet food formula, computer 104 can signal to factory 106 to choose a pre-made formulation (for example, kibble BGF2), computer 104 can signal to factory 106 to choose a pre-made formulation and add a pre-made topping, computer 104 can signal to factory 106 to choose a pre-made formulation and manufacture a topping and/or the like.

In another exemplary embodiment, and with reference to FIG. 10, pet profile information indicates that the pet is an adult beagle, that the pet owner does not prefer a grain-free pet formula, and that the pet has somewhat difficult digestion. Computer 104 uses this pet profile information and cross-references it with stored nutritional information and requirements related to the beagle breed, adult dogs, and digestion, as well as stored nutritional information related to its kibble formulations. Based on the above information, Computer 104 determines that the recommended formulation is a cluster B type formulation, comprising lamb (type B2) is selected that is appropriate for an adult, medium sized dog that has somewhat difficult digestion. In addition, in one embodiment, based on the kibble selected, a pre-manufactured topping is selected based upon one or more preferred health outcomes, for example, a topping rich in omega-6 fatty acids and zinc may be selected to help nourish skin and promote a healthy coat.

In one embodiment, an appropriate daily feeding amount is calculated based on the nutrient profile of the kibble and the "topping" selected, the weight of the dog, body condition, season of the year, snacking habit and/or the like. In one embodiment, based on stool analyses of a biological sample, a custom additive in a gravy form, including vegetable oil, Vitamin E, soluble fiber to help the high stool texture and discomfort, mixture of soluble and insoluble fiber and a palatant digest coating is created by mixing the ingredients for the pet. Both the pre-manufactured kibble and the customized additive are given to the owner with feeding instructions and a copy of the above report. In one embodiment, a copy of the pet profile and sample stool test is sent to a veterinarian.

In addition, computer 104 can be programmed to assemble the user input and nutritional data into printed material. In an exemplary embodiment, the printed material includes customized pet feeding and care information for the individual pet, along with an ingredient statement, guaranteed analysis of the pet food, and/or a product label. In alternative embodiments, the printed material may also include recommendations regarding the use of treats and supplements, exercise of the pet, veterinary care, and/or the like. Additionally, computer 104 can be programmed to manage ingredient and supplies inventories, to generate customer notices or reminders for food re-orders, pet birthday cards, veterinary visits, special promotions and/or the like.

In one embodiment, computer 104 determines the feeding instructions for each formula are based on the pet's weight, age and stored classification information regarding the ideal weight for that type of pet breed. For example, if the pet is described as an adult male Siamese cat that weighs 10 pounds, computer 104 determines, based on stored information, that the cat is underweight. As such, computer 104 calculates that the following exemplary recommended caloric count is advised per feeding:

$$165.75\times(\text{pet weight})^{0.6711}=165.75\times10^{0.6711}=777 \text{ calories}$$

The feeding instructions will then indicate that the cat should receive one feeding a day, and that the feeding should comprise 1.5 cups of pet food.

The above described methods for customizing pet foods and pet products provide a way for pet food manufacturers to address the individualized health and nutrition requirements, and preferences, of individual pets and their owners. For example, the customized pet food and pet products can be tailored to provide a desired nutritional balance for a pet of a specific age, gender and weight, at a particular time of year, and having a specific health problem, such as, for example, a food allergy. In one embodiment, application of the methods to electronic telecommunications and data processing devices enable pet food manufacturers to provide customized pet food to users located at numerous facilities or locations, including for example, homes, veterinary offices, retail grocers and retail pet stores. The customized pet food can be delivered to the user at the site of manufacture, or manufactured at a site remote from the user and shipped or mailed to the user.

While the invention has been described in terms of various specific embodiments, those skilled in the art will recognize that the invention can be practiced with modification within the spirit and scope of the claims.

The foregoing detailed description herein refers to the accompanying drawings, which show exemplary embodiments by way of illustration and best mode. While these exemplary embodiments are described in sufficient detail to enable those skilled in the art to practice the systems and methods described herein, it should be understood that other embodiments can be realized and that logical and mechanical changes can be made. Thus, the detailed description herein is presented for purposes of illustration only and not of limitation.

For the sake of brevity, conventional data networking, application development and other functional aspects of the systems (and components of the individual operating components of the systems) cannot be described in detail herein. Furthermore, the connecting lines shown in the various figures contained herein are intended to represent exemplary functional relationships and/or physical couplings between the various elements. It should be noted that many alternative and/or additional functional relationships and/or physical connections could be present in a practical system.

The present disclosure has been described in terms of functional block components, block diagrams, flow charts, optional selections and various processing steps. It should be appreciated that such functional blocks can be realized by any number of hardware and/or software components configured to perform the specified functions. For example, the system can employ various integrated circuit components (e.g., memory elements, processing elements, logic elements, look-up tables, and the like), which can carry out a variety of functions under the control of one and/or more microprocessors and/or other control devices. Similarly, the software elements can be implemented with any programming and/or scripting language such as C, C++, Java, COBOL, assembler, PERL, Visual Basic, SQL Stored Procedures, extensible markup language (XML), hypertext markup language (HTML), SDML, DHTML, HDML, VRML, with the various algorithms being implemented with any combination of data structures, objects, processes, routines and/or other programming elements. Further, it should be noted that the system could employ any number of conventional techniques for data transmission, signaling, data processing, network control, and the like.

Moreover, it will be understood that each functional block of the block diagrams and the flowchart illustrations, and combinations of functional blocks in the block diagrams and flowchart illustrations, respectively, can be implemented by computer program instructions. These computer program instructions can be loaded onto a general-purpose computer, special purpose computer, and/or other programmable data processing apparatus to produce a machine, such that the instructions that execute on the computer and/or other programmable data processing apparatus create means for implementing the functions specified in the flowchart block and/or blocks.

These computer program instructions can also be stored in a computer-readable memory that can direct a computer and/or other programmable data processing apparatus to function in a particular manner, such that the instructions stored in the computer-readable memory produce an article of Manufacture including instruction means that implement the function specified in the flowchart block and/or blocks. The computer program instructions can also be loaded onto a computer and/or other programmable data processing apparatus to cause a series of operational steps to be performed on the computer and/or other programmable apparatus to produce a computer-implemented process such that the instructions which execute on the computer and/or other programmable apparatus provide steps for implementing the functions specified in the flowchart block and/or blocks.

Accordingly, functional blocks of the block diagrams and flowchart illustrations support combinations of means for performing the specified functions, combinations of steps for performing the specified functions, and program instruction means for performing the specified functions.

As will be appreciated by one of ordinary skill in the art, the systems and methods disclosed herein can be embodied as a method, a data processing system, a device for data processing, and/or a computer program product. Accordingly, the disclosed systems and methods can take the form of an entirely software embodiment, an entirely hardware embodiment, and/or an embodiment combining aspects of both software and hardware. Furthermore, the disclosed systems and methods can take the form of a computer program product on a computer-readable storage medium having computer-readable program code means embodied in the storage medium. Any suitable computer-readable storage medium can be utilized, including hard disks, CD-ROM, optical storage devices, magnetic storage devices, and/or the like.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments of the systems and methods described herein are, for example, capable of operation in sequences other than those illustrated or otherwise described herein. Furthermore, the terms "comprises," "comprising," "include," "have," and/or any other variation thereof, are intended to cover a non-exclusive inclusion, such that a process, method, article, and/or apparatus that comprises a list of elements does not include only those elements but may include other elements not expressly listed and/or inherent to such process, method, article, and/or apparatus. Further, no element described herein is required unless expressly described as "essential" and/or "critical."

What is claimed is:

1. A method for customizing a pet food for a pet, the method comprising:
   obtaining, at a user interface, pet attributes and preferences to form pet profile information, wherein the pet attributes include at least one of a species, an activity level, a medical history, a breed, a gender, a breeding status, a feeding method, an age, a spayed/neutered status, a snack schedule, a biological sample, a body condition, a dental health, a coat information, a digestive health information and a weight of the pet, and wherein the preferences comprise at least one user or pet preference regarding an ingredient, a food form, a flavor, a protein source, a shape and a texture;
   correlating the pet profile information with stored nutritional information to determine wellness variables, each of the wellness variables is a nutritional claim associated with one of a plurality of health aspects comprising (i) weight and body condition, (ii) digestion, and (iii) at least one additional health aspect selected from the group consisting of brain and vision; teeth and bones; joint health and mobility; oral health; energy; and skin and coat;
   prioritizing the wellness variables relative to each other based on the pet profile information;
   determining a pet food formula based upon the prioritized wellness variables, the pet food formula comprises a basal portion formula, and the determining of the pet food formula comprises using the prioritized wellness variables to select the basal portion formula from a plurality of predetermined basal portion formulas, the plurality of predetermined basal portion formulas comprising a first basal portion formula comprising a first protein type, the first basal portion formula is selected for the pet when the wellness variable associated with the health aspect of weight and body condition is prioritized over the wellness variable associated with the health aspect of digestion; a second basal portion formula comprising a second protein type different than the first protein type, the second basal portion formula is selected for the pet when the wellness variable associated with the health aspect of digestion is prioritized over the wellness variable associated with the health aspect of weight and body condition; and a third basal portion formula comprising a third protein type different than the first and second protein types; and
   manufacturing the pet food according to the pet food formula.

2. The method of claim 1, wherein the obtaining of the pet information includes obtaining a biological sample from the pet, the biological sample comprising at least one of a saliva, a stool, a hair, a blood, a tissue and a DNA of the pet.

3. The method of claim 1, wherein the manufacturing of the pet food comprises:
   manufacturing a basal portion specified by the basal portion formula;
   using the prioritized wellness variables to select a supplemental portion formula from a plurality of predetermined supplemental portion formulas; and
   manufacturing a supplemental portion specified by the supplemental portion formula.

4. The method of claim 3, wherein the manufacturing of the supplemental portion comprises manufacturing at least one of a topping, a sauce, a coating, a thickener, a gravy, and a powder.

5. The method of claim 1, comprising:
   displaying on the user interface a recommended formulation based on the prioritized wellness variables;
   accepting user input on the user interface selecting the recommended formulation; and
   in response to the user input, using the recommended formulation as the pet food formula according to which the pet food is manufactured.

6. The method of claim 1, comprising:
   displaying on the user interface a recommended formulation based on the prioritized wellness variables;
   accepting user input on the user interface modifying the recommended formulation; and
   in response to the user input, using the modified formulation as the pet food formula according to which the pet food is manufactured.

7. The method of claim 6, wherein the modifying of the recommended formulation comprises changing at least one protein type thereof from a recommended protein type to a user-selected protein type, the recommended protein type and the user-selected protein type are different from each other and are individually selected from the group consisting of chicken, lamb and salmon.

8. The method of claim 6, wherein the pet food formula comprises a supplemental portion formula in addition to the basal portion formula, and the modifying of the recommend formulation comprises changing the supplemental portion formula.

* * * * *